(12) United States Patent
Adamy et al.

(10) Patent No.: US 9,205,037 B2
(45) Date of Patent: Dec. 8, 2015

(54) SINGLE PHASE DEPILATORY COMPOSITION

(75) Inventors: Steven T. Adamy, Lawrenceville, NJ (US); Lauren Ciemnolonski, Princeton, NJ (US)

(73) Assignee: CHURCH & DWIGHT CO., INC., Princeton, NJ (US)

( * ) Notice: Subject to any disclaimer, the term of this patent is extended or adjusted under 35 U.S.C. 154(b) by 255 days.

(21) Appl. No.: 13/186,618

(22) Filed: Jul. 20, 2011

(65) Prior Publication Data
US 2013/0022568 A1 Jan. 24, 2013

(51) Int. Cl.
*A61Q 9/04* (2006.01)
*A61K 8/46* (2006.01)
*A61K 8/81* (2006.01)

(52) U.S. Cl.
CPC ............. *A61K 8/46* (2013.01); *A61K 8/8129* (2013.01); *A61Q 9/04* (2013.01); *A61K 2800/5922* (2013.01)

(58) Field of Classification Search
None
See application file for complete search history.

(56) References Cited

U.S. PATENT DOCUMENTS

| 4,521,561 | A | * | 6/1985 | Hausman et al. ............. 524/459 |
| 5,200,175 | A | | 4/1993 | Tabata et al. |
| 5,665,338 | A | | 9/1997 | Tanimura et al. |
| 5,897,857 | A | | 4/1999 | Hillebrand et al. |
| 6,045,779 | A | | 4/2000 | Mueller et al. |
| 6,503,517 | B1 | | 1/2003 | Mohammadi et al. |
| 7,157,411 | B2 | | 1/2007 | Rohde et al. |
| 7,592,002 | B2 | | 9/2009 | Gupta |
| 2003/0096012 | A1 | * | 5/2003 | Besse et al. ................... 424/489 |
| 2003/0175333 | A1 | * | 9/2003 | Shefer et al. .................. 424/449 |
| 2004/0047830 | A1 | * | 3/2004 | Goldberg et al. ............... 424/73 |
| 2006/0269489 | A1 | * | 11/2006 | Adamy ............................ 424/59 |
| 2007/0031360 | A1 | * | 2/2007 | Gupta ......................... 424/70.11 |
| 2008/0138304 | A1 | | 6/2008 | Biggs et al. |
| 2008/0275138 | A1 | * | 11/2008 | Ridley et al. ............... 514/772.6 |
| 2009/0005462 | A1 | | 1/2009 | Gunn et al. |
| 2009/0068119 | A1 | | 3/2009 | Cawthorne |
| 2010/0083443 | A1 | | 4/2010 | Tindal et al. |

OTHER PUBLICATIONS

McKay, Polyquats as Conditioning Agents downloaded from Naturally Curly.com, written on Apr. 1, 2009.*

* cited by examiner

*Primary Examiner* — Michael G Hartley
*Assistant Examiner* — Nabila Ebrahim
(74) *Attorney, Agent, or Firm* — Fishman & Associates, LLC

(57) ABSTRACT

A depilatory composition, and a method of using a depilatory composition, where the present invention is a depilatory composition comprising: (1) a film-forming polymer; (2) depilatory active ingredients; and (3) a solvent system, wherein the depilation composition forms a peelable film after drying. The depilation composition of the present invention uses a blend of fully and partially hydrolyzed poly(vinyl alcohol).

13 Claims, 5 Drawing Sheets

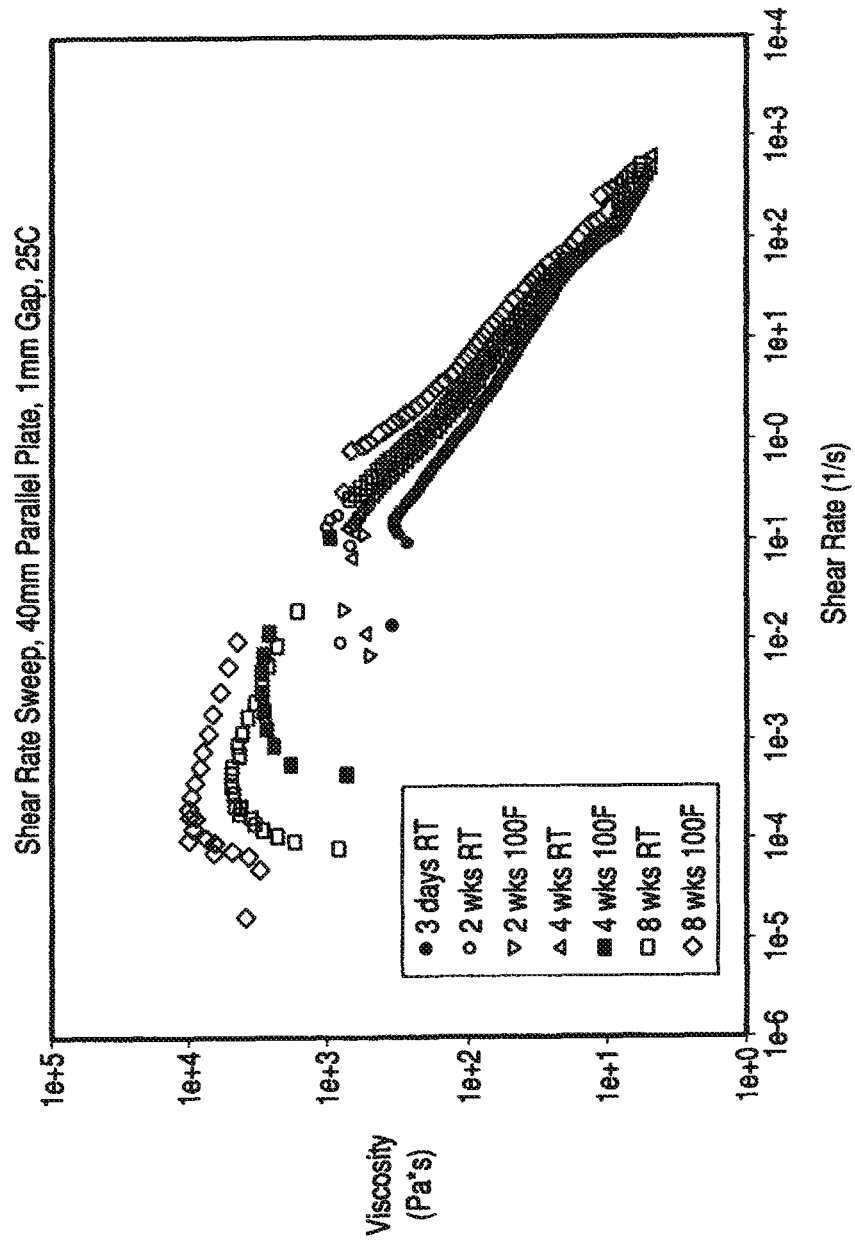

SINGLE PHASE DEPILATORY COMPOSITION

FIELD OF THE INVENTION

The invention relates to depilatory compositions which can be peeled away from the skin.

BACKGROUND OF THE INVENTION

As an alternative to shaving, many hair removal products available today perform through either chemical degradation (depilation) or mechanical removal (epilation) of the hair. Compositions for removing superfluous body hair are well known and are of various types. Currently on the market there are many different types of chemical depilatories and epilation products. Epilatory products, such as waxing, require initial heating before being applied to the skin in a generally molten state. It is then allowed to solidify before being removed from the skin together with unwanted hair.

One major drawback with waxing is the pain associated with hair removal. Waxing works by pulling the hair out from the roots. The hair follicle is surrounded by a small muscle that allows the hair to be erected in response to cold or excitement. Also attached with this muscle are nerve endings. These structures make pulling the hair out fairly hard and painful. The pain creates a fear associated with the waxing procedure which will cause many people not to repeat the procedure. Even if the person does repeat the waxing, the fear can cause the muscles to tense up, which in turn creates even more pain in subsequent procedures.

Chemical-based depilation offers an attractive alternative to waxing or shaving with the removal of hair being accomplished through the cleavage of disulfide bonds in the hair fiber as well as denaturation of the associated protein matrix. Unlike waxing, chemical-based depilation digests the hair and the hair is not pulled out, thus avoiding the pain associated with waxing. However, a relatively small proportion of individuals, compared with shaving, employ depilatories. One reason for the limited use may be that the hair cleavage reaction must be run at a very high pH. A typical example is the Nair® lotion product, having a pH of about 12.5 to 13.

Chemical-based depilatory compositions typically use a thiol-based depilatory agent, such as thioglycolic acid, for removal of unwanted body and facial hair and its use is well established in the art. These agents react by reducing hair's protein disulfide bonds to sulfhydryl anions, thereby allowing easy removal of the weakened hairs when washed or wiped away. However, in using thiols, it was discovered that certain conditions facilitated the effectiveness of this reaction. One such condition is high alkalinity to provide ionized reactants. Not only does the high pH (approximately 12.0-13) result in ionized thiols, but they also result in increased penetration of a reactant. Substances to provide further enhancement of penetration by active thiols were developed.

Currently on the market there are many different types of chemical depilatories. They range in form from creams to gel to aerosol mousses and spray products. Depilatory composition in the form of a cream is applied to the skin at room temperature. One drawback to many of these depilatory products is the required clean up. As discussed earlier, chemical depilatories contain a strong alkaline, usually a metal hydroxide. In addition, there is usually a reducing agent used. These chemicals can cause considerable damage to the skin if not properly removed. Likewise, they will quickly cause significant damage if they get into the eyes. Product wiped off the skin is still active and will corrode aluminum and many organic materials, creating the possibility of property damage or injury to the user, children or pets through inadvertent contact.

Products have been made to help reduce the risks associated with using these high pH depilatory products by trapping the dangerous chemicals in a solid matrix, i.e., a semi-solid film, after use, thereby simplifying disposal because there will not be liquid which can stick to surfaces. These depilatory products form a dry rubbery film on the skin which after a period of a few minutes can be peeled in one piece from the skin. In this manner, the product is similar to a hot wax depilation. After removal of the product, a very slight residue is left behind, which could be removed with a damp towel. However, unlike wax, the hair will have been digested by chemicals and not pulled out, thereby avoiding the pain associated with pulling out hair as in waxing. Further, there is the elimination of a great deal of mess. European Patent Application No. 0196896A2 to Hori et al. describes such a product.

European Patent Application No. 0196896A2 describes a depilatory composition comprising an aqueous solution or emulsion (e.g. a paste or gel) of a depilatory agent, a film-forming polymer (such as poly(vinyl alcohol)), which can be water-soluble or insoluble, and optionally an alkali hair swelling accelerating agent or a filler. The composition of European Patent Application No. 0196896A2 is spread on an area of skin having hair, the coating is allowed to dry naturally or by treating with hot air and/or absorbing water into an absorbent sheet pressed onto the film; and the film is peeled off with the hairs embedded therein, optionally with use of a pressure-sensitive adhesive sheet placed on the film.

In using these depilatory compositions, it is advantageous to have compositions which are capable of forming films when they are applied to the skin. Compositions having film-forming properties have the advantages of facilitating the removal of the depilatory composition from the skin and the ease of disposal of the depilatory composition along with the digested hairs simply by peeling off the dried composition.

The components imparting the above-noted film-forming properties are generally high-molecular-weight polymers. To obtain substantial film-forming properties in depilatory compositions, it is not satisfactory to simply increase the concentration of these high-molecular-weight polymers in the depilatory compositions. Such an approach is indeed limited by the fact that these film-forming polymers excessively increase the viscosity of the finished product. The finished product becomes too thick; it is thus difficult to apply to the skin and therefore preventing the user from being able to properly apply the depilatory composition.

It would be most useful to formulate a depilatory composition with substantial film-forming properties, but in such a way that the viscosity of depilatory composition is low enough to properly apply to the skin as a thin film prior to forming a film.

SUMMARY OF THE INVENTION

The present invention relates to a depilation composition and method for removing hair without causing pain. The depilation composition of the present invention comprises an aqueous solvent system containing a film-forming polymer compound and a depilatory agent wherein the depilation composition forms a peelable film after drying. The present invention also relates to a depilation method comprising coating the aforementioned depilatory composition onto an area of skin where hair is to be removed, drying the resulting coating to form a peelable film, and then peeling off the film.

The depilation composition of the present invention uses a blend of fully and partially hydrolyzed poly(vinyl alcohol).

BRIEF DESCRIPTION OF THE DRAWINGS

FIG. 6 is a plot of rheometery results over time of an embodiment of the present invention.

DETAILED DESCRIPTION OF THE INVENTION

Figure 1:
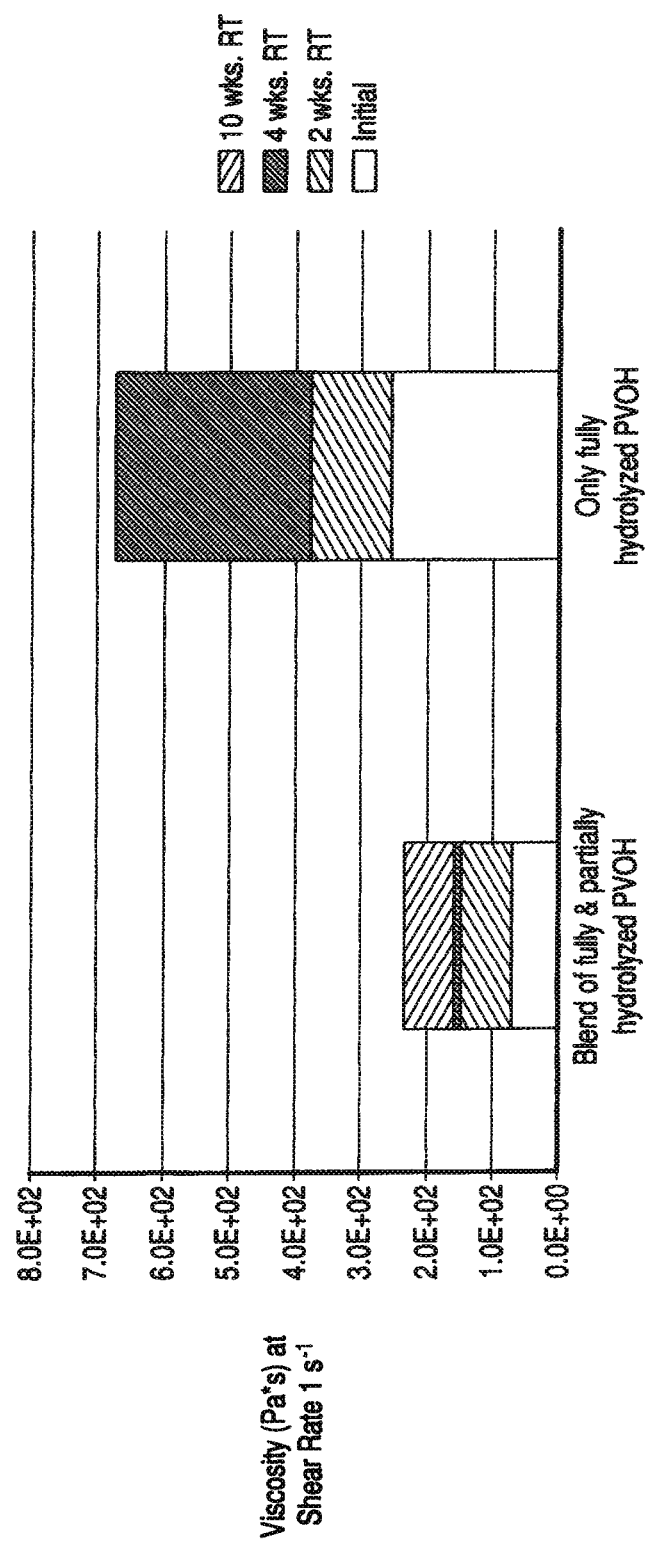
FIG. 1 is a chart of rheometery results over time for a depilatory composition containing a blend of fully and partially hydrolyzed PVOH and a depilatory composition containing only fully hydrolyzed PVOH.

The present inventors have now discovered that it is possible to overcome the above-noted disadvantages, i.e., to reinforce the film-forming properties of topical depilatory compositions without significantly increasing the viscosity of the finished product, by incorporating a blend of fully hydrolyzed (99+%) and partially hydrolyzed (87-88%) poly(vinyl alcohol).

Indeed, incorporating a blend of fully and partially hydrolyzed poly(vinyl alcohol) has now been found particularly capable of reinforcing the cohesion of a film formed by the depilatory composition. Their incorporation into the depilatory composition formulations has no damaging effects on their texture or to the viscosity of the finished product.

The present invention relates to a depilation composition and method for removing hair without causing pain. The depilation composition of the present invention comprises an aqueous solvent system containing a film-forming polymer compound and a depilatory agent wherein the depilation composition forms a peelable film after drying. The present invention also relates to a depilation method comprising coating the aforementioned depilatory composition onto an area of skin where hair is to be removed, drying the resulting coating to form a peelable film, and then peeling off the film.

The depilatory composition of the present invention comprises an aqueous solvent system containing a blend of fully and partially hydrolyzed poly(vinyl alcohol), which has a film-forming ability, a depilatory agent and may contain a film-reinforcing agent.

In another embodiment of the present invention, the depilatory composition further includes a film-reinforcing agent, such as methylcellulose or polyquaternium polymer.

In another embodiment of the present invention, the depilatory composition may further include an ionic salt to hinder the crosslinking of the polymer compound because if the polymer in the depilatory composition form crosslinks, such as when exposed to cold temperatures, the polymer forms a hydrogel and formation of these hydrogels is unfavorable because the product is not able to spread onto the skin and/or depilate as a hydrogel.

In another embodiment of the present invention, the depilatory composition may further include a polymeric emulsifier, such as acrylate/alkyl acrylate crosspolymers like Pemulen TR2 Acrylate Polymer (Lubrizol).

In another embodiment of the present invention, the depilatory composition may further include kaolin clay to improve the drying time of the composition and/or improve film integrity.

The depilatory compositions according to the present invention are in particular very effective when they are used as peelable packs, which are gels, preferably based on poly(vinyl alcohol) (or PVOH), which are spread in a layer on the skin and are removed simply by peeling off the dried film. The film-forming power of the depilatory composition ensures good cohesion of the film which is removed in a single piece and does not leave small fragments to be subsequently removed.

Film-Forming Polymer/s

The composition of the present invention includes one or a combination of water-soluble polymers which is able to form a peelable film upon drying. The film is sufficiently tough and resistant to breakage, allowing the film to be removed in one piece from the skin. The film-forming polymer of the present invention is poly(vinyl alcohol), particularly a blend of fully hydrolyzed (99+%) poly(vinyl alcohol) and partially hydrolyzed (~87-89%) poly(vinyl alcohol).

Depilatory formulations based on fully hydrolyzed poly(vinyl alcohol) encourage formulations that dry quickly to form durable films on the skin, however these formulations are unstable in terms of viscosity. On the other hand, formulations based on partially hydrolyzed poly(vinyl alcohol) are stable in terms of viscosity but increase dry time and sacrifice film integrity. It has been found that a blend of fully hydrolyzed (99+%) poly(vinyl alcohol) and partially hydrolyzed (87-89%) poly(vinyl alcohol) was found to create a formulation that dries quickly, forms a strong film and is fairly stable in terms of viscosity.

While not bound to any particular theory, it is believed that a blend of two polymers—one with a high degree of crystallinity (i.e., fully (99%) hydrolyzed PVOH) and a low degree of crystallinity (i.e., partially (88%) hydrolyzed PVOH) offer improved film toughness over a uniform film of intermediate crystallinity (i.e., 95% hydrolyzed). This would be due to the presence of distinct domains of "harder" and "softer" materials, much like a polymer composite. The more important factor here may be that by using a blend of the two materials, a convenient flexibility in formulating is available, where properties of the films are easily varied by adjusting the ratio of the two types of polymers. This allows one to tailor the film properties to specific requirements. For example, one may need to adjust the flowability of the product due to requirements of packaging. Increased flowability is attained by increasing the proportion of partially hydrolyzed material. Adjustments to other properties, e.g., toughness, dry time, adhesion, may also be adjusted by the ratio of the two materials.

Suitably, a film-forming polymer is provided in the depilatory composition in an amount of 0.1-30 wt %, preferably 2-15 wt % of the total weight of the composition. For depilatory compositions using a blend of fully and partially hydrolyzed PVOH, the fully hydrolyzed PVOH is provided in the depilatory composition in an amount of 0.50-15 wt %, preferably 1-5 wt % of the total weight of the composition; and the partially hydrolyzed PVOH is provided in the depilatory composition in an amount of 0.5-15 wt %, preferably 1-10 wt % of the total weight of the composition. The ratio of partially hydrolyzed poly(vinyl alcohol) to fully hydrolyzed poly(vinyl alcohol) can be from 1:4 to 4:1, preferably from 1:3 to 3:1.

Film-Reinforcing Agent

To further improve film integrity, the present invention may also include film-forming raw materials in the depilatory composition. Two such materials are hydroxypropyl methylcellulose (such as Dow Chemical's Methocel 40-202) and synthetic quaternary ammonium polymers.

Synthetic quaternary ammonium polymers, include film-forming polymers and conditioning polymers. Non-limiting examples of synthetic quaternary ammonium polymers include polymers and copolymers of dimethyl diallyl ammonium chloride, such as polyquaternium-4, polyquaternium-6, polyquaternium-7, polyquaternium-22, polyquaternium-10, polyquaternium-11, polyquaternium-15, polyquaternium-16, polyquaternium-24, polyquaternium-28, polyquaternium-32, polyquaternium-33, polyquaternium-35, polyquaternium-37, polyquaternium-39, polyquaternium-44, PEG-2-cocomonium chloride, quaternium-52, and the like.

In one embodiment of the present invention polyquaternium-11 (Rhodia's Mirapol PQ-11) is used as a film-reinforcing agent in the depilatory composition.

Suitably, a film-reinforcing agent is provided in the depilatory composition in an amount of 0.5-15 wt %, preferably 2-10 wt % of the total weight of the composition.

Depilatory Active Ingredients

The depilatory agent is a substance capable of degrading keratin. The active ingredients are used in order to denature the proteins in the hair causing it to swell by disrupting the hydrogen bonding in the protein chain. This disruption of the hydrogen bonding will open the protein up for easier attachment of the peptide bonds by hydroxide ions. The depilatory agent may be, for example, a sulphur compound such as potassium thioglycolate, dithioerythritol, thioglycerol, thioglycol, thioxanthine, thiosalicylcic acid, N-acetyl-L-cysteine, lipoic acid, $NaHSO_2$, $Li_2S$, $Na_2S$, $K_2S$, $MgS$, $CaS$, $SrS$, $BaS$, $(NH_4)_2S$, sodium dihydrolipoate 6,8-dithiooctanoate, sodium 6,8-dithiooctanoate, salts of hydrogen sulphide for example NaSH or KSH, thioglycolic acid, thioglycerol, 2-mercaptopropionic acid, 3-mercaptopropionic acid, thiomailic acid, ammonium thioglycolate, glyceryl monothioglycolate, monoethanolamine thioglycolate, monoethanolamine thioglycolic acid, diammonium dithiodiglycolate, ammonium thiolactate, monoethanolamine thiolactate, thioglycolamide, homocysteine, cysteine, glutathione, dithiothreitol, dihydrolipoic acid, 1,3-dithiopropanol, thioglycolamide, glycerylmonothioglycolate, thioglycolhydrazide, keratinase, hydrazine sulphate, hydrazine disulphate, triisocyanate, guanidine thioglycolate, hair reducing pack, calcium thioglycolate and/or cysteamine. Preferably, a depilatory composition comprises cysteamine.

Suitably, a depilatory agent is provided in the depilatory composition in an amount of 1-20 wt %, preferably 3-10 wt % of the total weight of the composition.

Solvent System

The solvent used in the composition is chosen from the compounds which solubilize or disperse at least the film-forming polymer. In the latter case, the film-forming polymers are in the form of dispersions of solid or liquid particles of polymer (latex or pseudolatex).

Examples of solvents that can be used in the present invention are water, ethanol, acetone, isopropanol, ethyl acetate, dichloromethane, ethyl ether and the like, and mixtures thereof.

The composition of the present invention is preferably applied to skin as a solution in a fugitive solvent which evaporates at a suitable rate when the composition is in contact with skin. Preferred examples of suitable solvents which solubilize the film-forming polymer and exhibit suitable volatility are isopropanol and ethanol.

Suitably, the composition comprises from 5 to 90% by weight of a solvent system. A solvent system can comprise a mixture of solvent and water and the solvent is provided in the depilatory composition in an amount of 3-40 wt %, preferably between 15-30 wt %, of the total weight of the composition with the balance of the solvent system being water.

pH Buffers

The depilatory composition of the present invention is alkaline, containing a salt to buffer the system at a higher pH. Examples of pH buffers include calcium hydroxide and sodium hydroxide. Due to the characteristics of the pH buffer, the depilatory composition maintains an alkaline pH. An alkaline environment is highly beneficial for the hair removal process. Desirably the pH of the composition of the present invention is at least 12.

Suitably, a pH buffer is provided in the depilatory composition in an amount of 1-20 wt %, preferably between 3-10 wt % of the total weight of the composition.

Crosslinking Hinderers

It has been noted in literature (i.e., Ma, R.; Xiong, D., Journal of China University of Mining and Technology 2008, 18, pp. 271-274) that formulations containing PVOH form crosslinks when exposed to cold temperatures (40F and below, but most notable at freezing temperatures), creating a hydrogel. For depilatory compositions like the depilatory composition of the present invention, formation of these cold-temperature-induced hydrogels is unfavorable because the composition is not able to spread onto the skin and/or depilate as a hydrogel. To hinder crosslink formation of the PVOH at lower temperatures, ionic salts can be added to the formulation of the present invention. One embodiment of the present invention incorporates sodium chloride as a crosslinking hinderer.

Suitably, a crosslinking hinderer may be provided in the depilatory composition in an amount of 0.1-10 wt %, preferably 0.5-3 wt % of the total weight of the composition.

Thickeners/Gel Strengthening Agents

Among the other ingredients useful in these various embodiments is a gelling agent or thickener, present at levels of from about 0% to about 30%. The thickeners used could include both natural and synthetic ones such as tragacanth, xanthan, karaya, and guar gums, clays, methyl or hydroxyethyl cellulose, hydroxypropyl cellulose, carboxymethyl cellulose, fatty and polyvinyl alcohols, modified starches and sugars, and mixtures thereof.

Materials can also be added to the formula to increase the strength of the set film. These have been a variety of materials. One of the most common and useful is kaolin clay. Kaolin is low in free cations. In efforts to create a thicker and easier to remove film, kaolin clay was incorporated into the present formulation. Kaolin clay successfully thickened the film formed on the skin and also slightly decreased the film dry time and increased film integrity.

Silica has been used to give the gel strength. Embodiments have included fumed silica and surface treated silicas.

Other agents can be used to control the properties of the hydrosol before gelling or to suspend the powder ingredients. These can be other polymers such as Carbomer or Xanthan gums. Pure viscosity control could be achieved through the use of non-ionic celluloses such as HEC or CMC. These will hydrolyze in the final mixture but may provide temporary needed viscosity control.

Specialty polymers that thicken on increased pH such as Stutture 2001 from Akzo Nobel may be of benefit.

Suitably, a thickener, such as kaolin clay, may be provided in the depilatory composition in an amount of 0-10 wt %, preferably 2-6 wt % of the total weight of the composition. A thickener such as silica may also be provided in the depilatory composition in an amount of 0-2 wt %, preferably 0.1-0.5 wt % of the total weight of the composition Polymeric Emulsifiers In the present invention, it is preferable to blend in a polymeric emulsifier, such as an acrylic acid methacrylic acid alkyl polymer, in view of long-term stability. Polymeric emulsifiers that may be used in the present invention include, but are not limited to: acrylates/alkyl acrylates crosspolymers; acrylates/acryamide acrylates copolymers; mixtures thereof; and, the like.

Examples of polymeric emulsifers that may be used in the present invention include, but are not limited to: acrylate/alkyl acrylate crosspolymers sold under the trade designation of Pemulen; hydroxypropyl starch phosphate 7; mixtures thereof; and, the like. Some examples of such crosspolymers and copolymers include, but are not limited to: acrylate/$C_{10}$-$C_{30}$ alkyl acrylate crosspolymers; acrylate/acrylamide copolymers; hydroxypropyl starch phosphate; mixtures thereof; and, the like.

A composition of the present invention which has superior long term stability can be obtained by adding an acrylic acid methacrylic acid alkyl polymer. The type of the acrylic acid methacrylic acid alkyl polymer is not limited in particular. For example, Pemulen TR-2 (from B.F. Goodrich company), which is commercially available, can be used.

Suitably, a polymeric emulsifier is provided in the depilatory composition in an amount of 0.25-3 wt %, preferably 0.5-2 wt % of the total weight of the composition.

Other Ingredients

Emollients

The depilatory composition of the present invention may additionally include an emollient. Emollients include stearyl alcohol, mink oil, cetyl alcohol, oleyl alcohol, isopropyl laurate, polyethylene glycol, petroleum jelly, palmitic acid, oleic acid, and glycerin.

Suitably, an emollient can be provided in the depilatory composition in an amount of 0-15 wt %, preferably 2-10 wt % of the total weight of the composition.

Skin Protecting Agent

As with all depilatories a skin protecting agent may be added to the formula. Most preferred is to use dimethicone for this function. It provides an occlusive barrier that can help to protect the skin from the caustic active ingredients. 0.5-2.0% should be sufficient. It is important to not use excessive amounts of a skin protectant like dimethicone or petrolatum because they can coat the hair preventing attachment of the protein chain.

Humectant/Moisturizers

The depilatory composition of the present invention may additionally include one or more oils. The oil may act as a moisturizer and/or humectant. Suitable oils include allantoin, shea butter, cocoa butter, goa butter, kukui nut oil, coconut oil, castor oil, palm oil, olive oil, avocado oil, apricot kernel oil, sweet almond oil and hemp oil. Other oils include mineral oils (e.g. paraffin oil), isohexane and sunflower seed oil. Preferably, the composition includes mineral oil.

The oil may be present in the composition in an amount 0.01% to about 1.5% by weight of the composition, preferably in an amount less than about 1.0% by weight, further preferably less than about 0.1% by weight of the composition.

Odor Masks and Fragrances

Although not necessary to the formulation, special attention must be paid to the fragrances. Most fragrances are not stable to high pH systems. Some fragrances at this pH seem to cause a crosslinking or complexing with the polyvinyl alcohol because on their addition the polymer phase quickly turns to rubber. An example of a fragrance that can be used in the present invention is Fragrance RR-1204 (Takasago).

Suitably, a fragrance may be provided in the depilatory composition in an amount of 0-1 wt %, preferably 0.25-0.75 wt % of the total weight of the composition.

Chelating Material

The addition of ethylenediaminetetraacetic acid (EDTA) may be important because thioglycollates may complex with any free iron and turn a purple color.

Colorants

Colorants are not necessary to the formulation but may be used for commercial appeal.

EXAMPLES

With the necessary and optional ingredients thus described, an exemplary embodiment of the depilatory composition of the present invention, with each of the components set forth in weight percent, are shown in the tables below.

Example 1

FIG. 1 illustrates the improved viscosity stability over 10 weeks at room temperature of an embodiment of the present invention that utilizes a blend of fully and partially hydrolyzed poly(vinyl alcohol) compared to a formulation based only on fully hydrolyzed poly(vinyl alcohol). As can be seen in FIG. 1, the blend of fully and partially hydrolyzed PVOH maintains a relatively low viscosity at shear rate of 1 $s^{-1}$ even after 10 weeks. In comparison, the viscosity of a composition containing only fully hydrolyzed PVOH, even after four weeks, increases significantly and becomes unusable.

Table 1 shows the components of the two formulations used in FIG. 1.

TABLE 1

Formulations using either fully hydrolyzed PVOH or a blend of fully hydrolyzed and partially hydrolyzed PVOH.

| | Weight % | |
|---|---|---|
| Sample | A | B |
| Fumed silica (Cab-o-sil HS-5) (Cabot) | 0.25 | 0.20 |
| PVOH 99+% hydrolyzed MW = 146-186K | 7.50 | 3.50 |
| PVOH 87-89% hydrolyzed MW = 146-186K | 0 | 3.50 |
| Pemulen TR2 Acrylate Polymer (Lubrizol) | 1.25 | 1.50 |
| In-Situe acrylic copolymer (Dow) | 0.00 | 1.50 |
| Mirapol PQ-11 (Rhodia) (19-21% solids in water) | 0.00 | 5.00 |
| AQ55S Polymer (Eastman) | 5.00 | 0.00 |
| Glycerin | 5.00 | 5.00 |
| 2-propanol | 20.00 | 20.00 |
| Calcium Hydroxide | 5.00 | 5.00 |
| Cysteamine-HCl | 5.00 | 5.00 |
| Deionized $H_2O$ | 51.00 | 49.80 |

Figure 2:
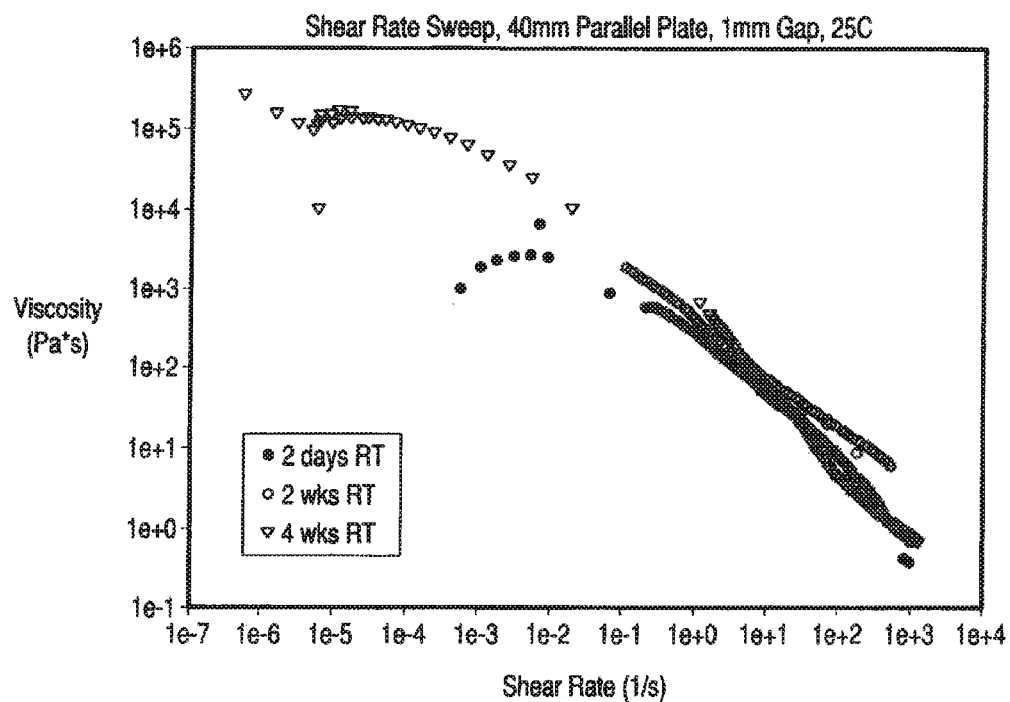
FIG. 2 is a plot of rheometery results over time of a depilatory composition containing fully hydrolyzed PVOH.
Figure 3:
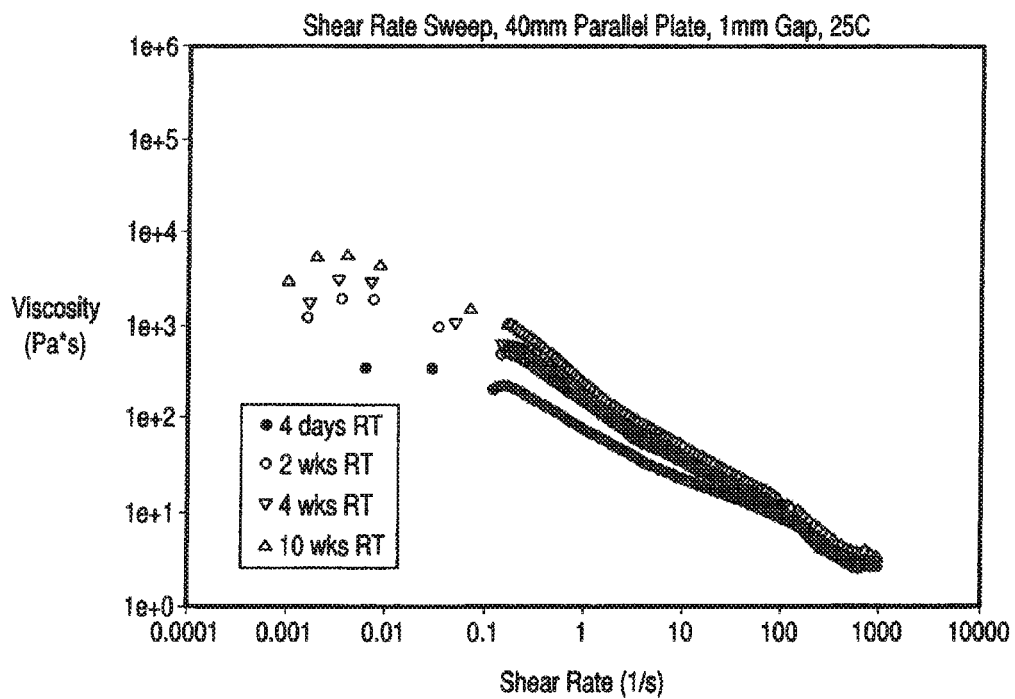
FIG. 3 is a plot of rheometery results over time of a depilatory composition containing a blend of fully and partially hydrolyzed PVOH.

Full rheology plots can be seen in FIGS. 2 and 3. FIG. 2 illustrates the stability of the viscosity of the depilatory composition containing only fully hydrolyzed PVOH. FIG. 3 illustrates the stability of the viscosity of the depilatory composition containing a blend of fully and partially hydrolyzed PVOH. From FIGS. 2 and 3, one can see that the initial viscosity of the depilatory composition containing the blend (Sample B) is lower than that of the depilatory composition containing only fully hydrolyzed PVOH (Sample A). Furthermore, the rheology of Sample B is much more stable over the entire shear range even after 10 weeks at room temperature.

Example 2

Table 2 shows the components of four formulations with varying ratios of fully hydrolyzed and partially hydrolyzed PVOH and Ca(OH)$_2$ according to the present invention.

TABLE 2

Compositions containing fully and partially hydrolyzed PVOH blends

| | Weight % | | | |
|---|---|---|---|---|
| Sample # | 1 | 2 | 3 | 4 |
| Fumed silica (Cab-o-sil HS-5) (Cabot) | 0.20 | 0.20 | 0.20 | 0.20 |
| PVOH 99% hydrolyzed MW = 181K | 5.625 | 3.75 | 5.625 | 3.75 |
| PVOH 87% hydrolyzed MW = 181K | 1.875 | 3.75 | 1.875 | 3.75 |
| Pemulen TR2 Acrylate Polymer (Lubrizol) | 1.49 | 1.49 | 1.49 | 1.49 |
| Ca(OH)2 | 0.00 | 0.00 | 5.00 | 5.00 |
| AQ48 Polyester Polymer (Eastman) | 3.00 | 3.00 | 3.00 | 3.00 |
| Glycerin | 5.00 | 5.00 | 5.00 | 5.00 |
| 2-propanol | 20.00 | 20.00 | 20.00 | 20.00 |
| KOH | 5.50 | 5.50 | 1.00 | 1.00 |
| K$_3$PO$_4$ | 2.00 | 2.00 | 0.00 | 0.00 |
| Cysteamine-HCl | 5.00 | 5.00 | 5.00 | 5.00 |
| Deionized H$_2$O | q.s. | q.s. | q.s. | q.s. |

The compositions were evaluated for stability by storing the samples for 1 week at both room temperature and at 40° C. Viscosity values were assessed via a rheometer using 40 mm diameter parallel plate geometry. The viscosity results showed that samples 1, 3 and 4 displayed similar behaviors. Viscosity levels increased after one week in both room temperature and 40° C. samples. In the higher shear regions, viscosity differences were minor. For sample 2, the 40° C. sample displayed significant increases in viscosity over the shear range.

Viscosity levels were assessed in samples 3 and 4 at 13 days as well. In general, there were no significant increases in viscosity from one week to 13 days. The viscosity values for both the samples exposed at 40° C. actually appeared to decrease (closer to the initial value) between one week and 13 days.

The compositions illustrated in Table 2 were also assessed for performance by applying to a leg with hair. Table 3 shows the performance of the formulations.

TABLE 3

Performance of compositions of Table 2

| Sample # | Approximate Dry Time (min) | Comments |
|---|---|---|
| 1 | 14 | Film has low structural integrity, hair removed. |
| 2 | 18 | Film tougher than sample 1, generally removed in one piece, 90-95% hair removed |
| 3 | 20 | Film removed in some pieces, hair removal good |
| 4 | 19 | Film removable in large sections, good removal. |

In general, samples 2 and 4 showed better film integrity. These samples had higher proportions of fully hydrolyzed polyvinyl alcohol.

Example 3

As described above, an embodiment of the present invention can further include film-reinforcing agents to improve film integrity. Formulations containing hydroxypropyl methylcellulose and polyquaternium-11 as film-reinforcing agents were made and did in fact demonstrate an increase in film integrity. Table 4 illustrates two formulations of the present invention in which one formulation (Sample C) does not contain a film-reinforcing agent while the second formulation (Sample D) contains polyquaternium as a film reinforcing agent.

TABLE 4

Two formulations of the present invention — one without a film-reinforcing agent and one with polyquaternium as a film reinforcing agent

| Raw Material | Sample C | Sample D |
|---|---|---|
| | Weight % | |
| Cab-o-sil HS-5 Fumed Silica (Cabot) | 0.25 | 0.20 |
| Poly(vinyl alcohol), MW 146-186K, 99+% hydrolyzed (Aldrich) | 1.75 | 1.75 |
| Poly(vinyl alcohol), MW 146-186K, 87-89% hydrolyzed (Aldrich) | 5.25 | 5.25 |
| Pemulen TR2 Acrylate Polymer (Lubrizol) | 1.50 | 1.50 |
| In-Situe acrylic copolymer (Dow) (47.5% solids polymer dispersion) | 1.50 | 1.50 |
| Mirapol PQ-11 (Rhodia) (19-21% solids in water) | 0.00 | 5.00 |
| Glycerin | 5.00 | 5.00 |
| 2-Propanol | 20.00 | 20.00 |
| Calcium Hydroxide | 5.00 | 5.00 |
| Cysteamine-HCl | 5.00 | 5.00 |
| Deionized H$_2$O | 54.75 | 49.80 |

Table 5 illustrates two formulations of the present invention in which one formulation (Sample E) does not contain a film-reinforcing agent while the second formulation (Sample F) contains hydroxypropyl methylcellulose as a film reinforcing agent.

TABLE 5

Two formulations of the present invention — one without a film-reinforcing agent and one with hydroxypropyl methylcellulose as a film reinforcing agent

| Raw Material | Sample E | Sample F |
|---|---|---|
| | Weight % | |
| Cab-o-sil HS-5 Fumed Silica (Cabot) | 0.200 | 0.200 |
| Poly(vinyl alcohol), MW 146-186K, 99+% hydrolyzed (Aldrich) | 1.875 | 1.875 |
| Poly(vinyl alcohol), MW 146-186K, 87-89% hydrolyzed (Aldrich) | 5.625 | 5.625 |
| Pemulen TR2 Acrylate Polymer (Lubrizol) | 1.449 | 1.449 |
| AQ-48 Polyester Polymer (Eastman) | 3.000 | 3.000 |
| Methocel 40-202 (Dow) | 0.000 | 0.200 |
| Glycerin | 5.000 | 5.000 |
| 2-Propanol | 20.000 | 20.000 |
| Calcium Hydroxide | 5.000 | 5.000 |
| Potassium Hydroxide | 1.000 | 1.000 |
| Cysteamine-HCl | 5.000 | 5.000 |
| Deionized H$_2$O | 51.850 | 51.650 |

Figure 4:
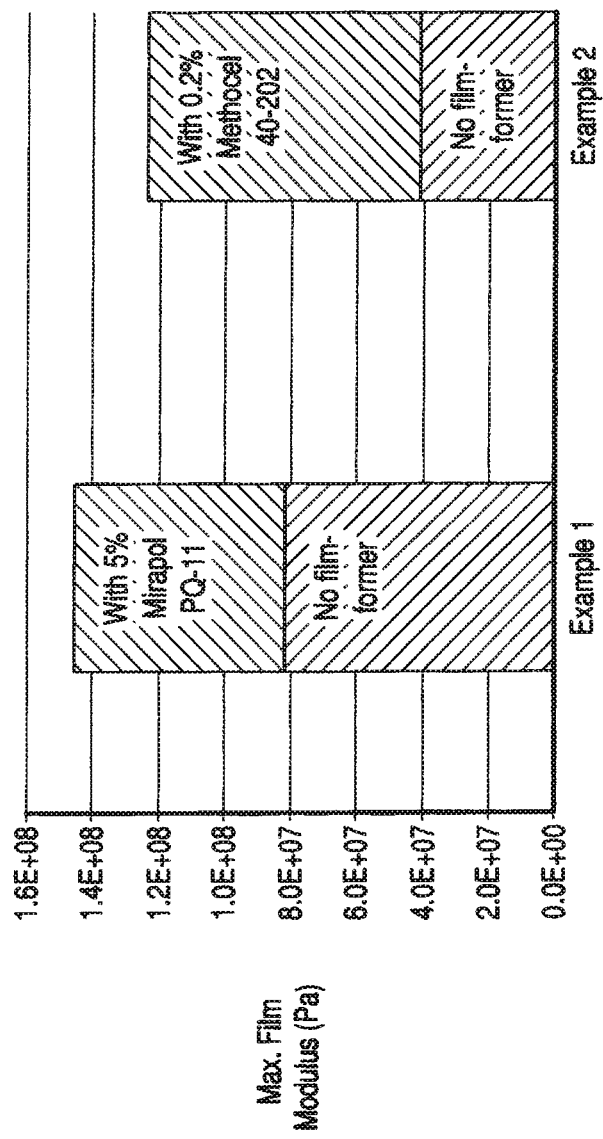
FIG. 4 is a chart illustrating an increase in film modulus of depilatory compositions containing film-reinforcing agents.

FIG. 4 shows the increase in film modulus of completely dried depilatory formulation films containing these film-reinforcing agents compared to the same formulations containing no film-reinforcing agents. As can be seen in FIG. 4, the maximum film modulus of Sample C containing no film-reinforcing agent is about $8.0 \times 10^7$ Pa, but with 5% Mirapol PQ-11 (Sample D) included in the formulation, the maximum film modulus increased to over $1.4 \times 10^8$ Pa. In addition, FIG.

4 shows that the maximum film modulus of Sample E containing no film-reinforcing agent is about $4.0 \times 10^7$ Pa, but with 0.2% Methocel 40-202 (Sample F) included in the formulation, the maximum film modulus increased to over $1.2 \times 10^8$ Pa.

Example 4

An embodiment of the present invention, which includes polyquaternium as a film-reinforcing agent and includes kaolin clay as a thickener, was made. Table 6 shows the components of an embodiment of the present invention.

TABLE 6

Formulation of an embodiment of the present invention which includes Mirapol

| Ingredient | Weight % |
| --- | --- |
| Cab-o-sil HS-5 Fumed Silica (Cabot) | 0.20 |
| PVOH, MW 146-186K, 99+% hydrolyzed (Aldrich), 15% active solution in water | 23.33 |
| PVOH, MW 146-186K, 87-89% hydrolyzed (Aldrich), 17.5% active solution in water | 20.00 |
| Pemulen TR2 Acrylate Polymer (Lubrizol) 10% active solution in 2-propanol | 15.00 |
| In-Situe acrylic copolymer (Dow) (47.5% solids polymer dispersion) | 1.50 |
| Mirapol PQ-11 (Rhodia) (19-21% solids in water | 5.00 |
| Glycerin | 5.00 |
| Kaolin Clay | 5.00 |
| 2-Propanol | 6.50 |
| Calcium Hydroxide | 5.00 |
| Cysteamine-HCl | 5.00 |
| Deionized H₂O | q.s. |

The formulation in Table 6 was applied to a leg with hair in a thin layer (roughly 0.5 millimeters thick). After 10 minutes at room temperature, the formulation had dried into a peelable solid, which when removed gave good hair removal. The film was easy to remove and pain-free.

Example 5

Embodiments of the present invention, one of which incorporates a crosslinking hinderer, were made. Table 7 illustrates the components of two formulations of the present, one incorporating an ionic salt to hinder crosslink formation and one without an ionic salt.

TABLE 7

Formulations of the present invention — one containing an ionic salt and one without an ionic salt

| Sample # Ingredient | 3776-47-3 Weight % | 3776-65-2 Weight % |
| --- | --- | --- |
| Cab-o-sil HS-5 Fumed Silica (Cabot) | 0.2 | 0.2 |
| PVOH, MW 146-186K, 99+% hydrolyzed (Aldrich) | 3.5 | 3.5 |
| PVOH, MW 146-186K, 87-89% hydrolyzed (Aldrich) | 3.5 | 3.5 |
| Pemulen TR2 Acrylate Polymer (Lubrizol) | 1.5 | 1.5 |
| Kaolin Clay | 5.0 | 5.0 |
| Gafquat 755N Polyquaternium-11(ISP) (19-21% solids in water) | 5.0 | 5.0 |
| Glycerin | 5.0 | 5.0 |
| 2-Propanol | 20.0 | 20.0 |
| Calcium Hydroxide | 5.0 | 5.0 |
| Cysteamine-HCl | 5.0 | 5.0 |
| Sodium Chloride | 0.0 | 1.0 |
| Fragrance RR-1204 (Takasago) | 0.5 | 0.5 |
| Deionized H₂O | 45.8 | 44.8 |

Figure 5:
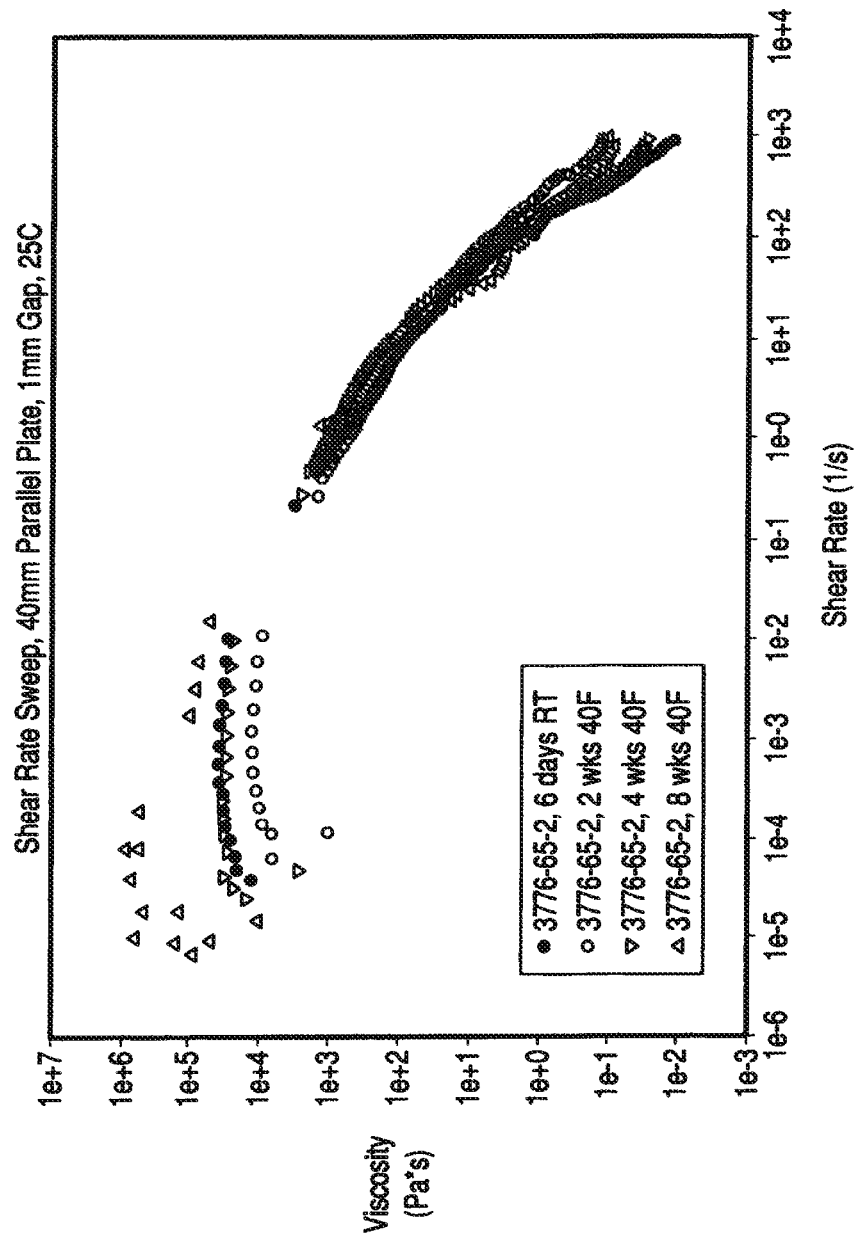
FIG. 5 is a plot of rheometery results over time of a depilatory composition containing a crosslinking hinderer.

FIG. 5 illustrates the rheology at 25° C. of the formulation containing the ionic salt following aging at 40° F. over 8 weeks. Rheology measurements of the samples that did not contain the ionic salt could not be obtained because the samples were too viscous. The incorporation of 1.0% sodium chloride appears to have considerably helped to hinder crosslink formation and thus improve viscosity stability at 40° F. over 8 weeks.

Example 6

Another embodiment of the present invention can be seen in Table 8.

TABLE 8

Formulation of an embodiment of the present invention

| Ingredient | Weight % |
| --- | --- |
| Cab-o-sil HS-5 Fumed Silica (Cabot) | 0.20 |
| PVOH, MW 146-186K, 99+% hydrolyzed (Aldrich) | 2.30 |
| PVOH, MW 146-186K, 87-89% hydrolyzed (Aldrich) | 4.70 |
| Pemulen TR2 Acrylate Polymer (Lubrizol) | 1.50 |
| Kaolin Clay | 5.00 |
| Gafquat 755N Polyquaternium-11 (ISP) (19-21% solids in water) | 5.00 |
| Fragrance RR-1204 (Takasago) | 0.50 |
| Glycerin | 5.00 |
| 2-Propanol | 6.50 |
| Calcium Hydroxide | 5.00 |
| Cysteamine-HCl | 5.00 |
| Deionized H₂O | 45.80 |

Rheology of the formulation can be seen in FIG. 6. The pH, viscosity, appearance, and product performance over time is summarized in Table 9.

TABLE 9

Summary of pH, viscosity, appearance and product performance of an embodiment of the present invention

| Age/ Conditions | pH | Viscosity (Pa*s) at Shear Rate 1 s-1 | Appearance | Film Dry Time (min.) on Skin* | Depilation Results |
| --- | --- | --- | --- | --- | --- |
| Initial | 11.63 | 122 | Thick, creamy, off-white paste | 12-18 | Good |
| 2 wks RT | 12.31 | 192 | Thick, creamy, off-white paste | 6-8 | Good |
| 2 wks 100 F. | 12.27 | 195 | Thick, creamy, off-white paste | 7-9 | Good |
| 4 wks RT | 11.81 | 196 | Thick, creamy, off-white paste | 12-14 | Good |
| 4 wks 100 F. | 11.69 | 255 | Thick, creamy, off-white paste | 12-14 | Good |

*when applied as a thin, even layer

Whereas particular embodiments of the present invention have been described for the purposes of illustration, variations may suggest themselves to those skilled in the art without departing from the invention as claimed.

We claim the following:

1. A liquid depilatory composition comprising:
 a) a film-forming polymer, wherein the film-forming polymer is a blend of fully hydrolyzed and partially hydrolyzed poly(vinyl alcohol);
 b) a depilatory active ingredient selected from potassium thioglycolate, thioglycerol, thiosalicylcic acid, thioglycolic acid, ammonium thioglycolate, glyceryl monothioglycolate, glycerylmonothioglycolate, calcium thioglycolate and cysteamine;

c) solvent system; and d) a thickener, wherein a thickener is selected from xanthan gum, methyl or hydroxyethyl cellulose, carboxymethyl cellulose, silica, kaolin clay, and mixtures thereof wherein the depilatory composition forms a peelable film after drying, wherein said fully hydrolyzed poly(vinyl alcohol) is in the amount of 0.5-5 wt. % of the overall depilatory composition and said partially hydrolyzed poly(vinyl alcohol) is in the amount of 0.5-10 wt. % of the overall depilatory composition.

2. The composition of claim 1 wherein the ratio of partially hydrolyzed poly(vinyl alcohol) to fully hydrolyzed poly(vinyl alcohol) is from 1:3 to 3:1.

3. The composition of claim 1 further comprising a film-reinforcing agent.

4. The composition of claim 3 wherein said film-reinforcing agent is hydroxypropyl methylcellulose or polyquaternium.

5. The composition of claim 3 wherein said film-reinforcing agent is polyquaternium-11 and is present in an amount of 0.5-15 wt. % of the overall depilatory composition.

6. The composition of claim 1 wherein said depilatory active ingredient is cysteamine hydrochloride.

7. The composition of claim 1 further comprising a crosslinking hinderer.

8. The composition of claim 7 wherein said crosslinking hinderer is an ionic salt.

9. The composition of claim 8 wherein said ionic salt is sodium chloride.

10. The composition of claim 1 wherein said thickener is present in the amounts up to 10 wt. % of the overall depilatory composition.

11. The composition of claim 1 further comprising an acrylate/alkyl acrylate crosspolymer.

12. The composition of claim 1 further comprising a pH buffer to provide a pH of at least 11.0.

13. The composition of claim 12 wherein said pH buffer is calcium hydroxide.

* * * * *